United States Patent
Amara et al.

(10) Patent No.: US 6,731,380 B2
(45) Date of Patent: May 4, 2004

(54) METHOD AND APPARATUS FOR SIMULTANEOUS MEASUREMENT OF THE REFRACTIVE INDEX AND THICKNESS OF THIN FILMS

(75) Inventors: Mohamed Kamel Amara, Dover, DE (US); Noureddine Melikechi, Dover, DE (US); Sabbir M. Mian, Westminster, MD (US)

(73) Assignee: Applied Optics Center of Delaware, Inc., Dover, DE (US)

(*) Notice: Subject to any disclaimer, the term of this patent is extended or adjusted under 35 U.S.C. 154(b) by 182 days.

(21) Appl. No.: 09/883,512

(22) Filed: Jun. 18, 2001

(65) Prior Publication Data

US 2003/0025899 A1 Feb. 6, 2003

(51) Int. Cl.[7] .................. G01H 21/00; G01H 21/41; G01B 11/28
(52) U.S. Cl. .................. 356/73; 356/128; 356/630
(58) Field of Search .................. 356/73, 128, 630; 250/559.27

(56) References Cited

U.S. PATENT DOCUMENTS

| | | | |
|---|---|---|---|
| 3,873,209 A | 3/1975 | Schinke et al. | 356/135 |
| 4,266,875 A | 5/1981 | Bodlaj | 356/381 |
| 4,660,980 A | 4/1987 | Takabayashi et al. | 356/357 |
| 4,672,196 A * | 6/1987 | Canino | 250/225 |
| 4,792,227 A | 12/1988 | Yoshizawa | 356/128 |
| 4,924,105 A | 5/1990 | Nagao | 250/560 |
| 4,983,823 A | 1/1991 | Isobe | 250/225 |
| 5,034,617 A | 7/1991 | Isobe | 250/560 |
| 5,096,298 A | 3/1992 | Isobe | 356/369 |
| 5,114,235 A * | 5/1992 | Suda et al. | 356/401 |
| 5,125,740 A | 6/1992 | Sato et al. | 356/128 |
| 5,237,392 A | 8/1993 | Hickel et al. | 356/381 |
| 5,400,144 A | 3/1995 | Gagnon | 356/382 |
| 5,420,680 A | 5/1995 | Isobe et al. | 356/128 |
| 5,541,733 A | 7/1996 | Gagnon | 356/382 |
| 5,630,423 A | 5/1997 | Wang et al. | 128/664 |
| 5,631,171 A | 5/1997 | Sandstrom et al. | 436/518 |
| 5,663,708 A * | 9/1997 | Strawn | 340/465 |
| 5,943,134 A | 8/1999 | Yamaguchi et al. | 356/357 |
| 6,057,928 A | 5/2000 | Li et al. | 356/445 |
| 6,091,485 A | 7/2000 | Li et al. | 356/73 |
| 6,130,439 A | 10/2000 | Le Menn | 250/573 |
| 6,172,752 B1 * | 1/2001 | Haruna et al. | 356/503 |
| 6,549,291 B1 * | 4/2003 | Dieter et al. | 356/630 |

FOREIGN PATENT DOCUMENTS

WO  WO 200026665 A1 * 5/2000 ......... G01N/21/55

\* cited by examiner

Primary Examiner—Zandra V. Smith
Assistant Examiner—Gordon J. Stock, Jr.
(74) Attorney, Agent, or Firm—RatnerPrestia

(57) ABSTRACT

A beam deflection technique for simultaneous measurements of the thickness, refractive index and optical absorption of transparent materials using a charge coupled device (CCD) camera is provided. The method comprises measuring beam deflection after transmission through or reflection off a sample of interest at variable incidence angles to the sample surface. The measurement of beam deflection as a function of incident angle is related through Snell's Law directly to the sample thickness and sample index of refraction.

19 Claims, 4 Drawing Sheets ns system lab and other a standard sources to and to be the refractive index. this direction is the photo of the index as and light to be very reflective for film matrix to much at $p$ <= .005.

METHOD AND APPARATUS FOR SIMULTANEOUS MEASUREMENT OF THE REFRACTIVE INDEX AND THICKNESS OF THIN FILMS

TECHNICAL FIELD

The present invention relates to a beam deflection technique for simultaneous measurements of the thickness, refractive index and optical absorption of transparent materials using a charge coupled device (CCD) camera. The method and apparatus is particularly suited to measuring flat, thin materials.

BACKGROUND OF THE INVENTION

Many optical devices such as spectrophotometers use absorption spectroscopy to measure the concentration of various materials. There are two primary procedures used for measuring concentration. An absorption value of a material is calculated at an absorbing wavelength and the absorption of the material at a minimally absorbing wavelength is subtracted. This process of "blanking" minimizes uncertainties due to sample cell imperfections and parasitic scattering. Another procedure involves taking absorption measurements on a material at various time intervals and analyzing the differences between measurements. In these methods, as well as in other technologies such as scattering techniques and optical cavity based techniques, the accurate knowledge of the refractive index of the material and optical path length is critical information.

In these methods of concentration measurement, the reflectivity losses due to the index of refraction are generally assumed to be a function only of wavelength. This assumption introduces uncertainties in absorption measurements because the refractive index also directly depends on the number density and the type of polarizable species in the material. As a result, there is a need to develop techniques to measure accurately refractive indices of samples at the specific optical absorption wavelength.

Accurate thickness (optical path length) data for a given material greatly enhances the sensitivity and accuracy of spectrophotometers and other absorption devices in concentration measurement. Furthermore, the need to accurately monitor and control the refractive index and thickness of samples during production exists in the manufacturing of materials such as laboratory windows, optical lenses, automotive parts, and optical glasses.

The refractive index and optical path are measured by a method described in U.S. Pat. No. 6,057,928, issued to Li et al. This technique measures the variations in reflectance (ratio of the reflected beam over the incident beam powers) and the beam phase distribution as a function of the incidence angle of a far IR beam on a film. Using Fresnel equations relating the reflectance and the phase of a beam to the incidence angle and the refractive index, the refractive index of a film is estimated. The refractive index is determined by fitting the experimental reflectance and phase variation curves to the theoretical Fresnel equations.

The method in the '928 patent uses GHz-THz radiation sources in the far IR region. These sources have wavelengths of 0.1 mm to 1 cm, and therefore the technique is available for materials of a few microns in thickness. The method described in the '928 patent uses a femtosecond mode-locked laser to excite an emitter, and a sophisticated detection mechanism.

The need remains for a cost-effective technique that provides for the simultaneous measurement of the refractive index and thickness of various film materials.

SUMMARY OF THE INVENTION

The present invention provides a method for the simultaneous determination of sample thickness L and index of refraction n. The method comprises forming a sample with first and second surfaces. A radiation beam is also formed and the radiation beam impinges onto the sample at an incidence angle ($A_1$) relative to the perpendicular axis to the first surface. The method also includes reflecting the impinged radiation beam from the first and second surfaces of the sample to form first and second reflected radiation beams. The first and second reflected radiation beams then impinge on a detection device which allows the measurement of the distance ($d_1$) on the detector between the impingement point of the first reflected beam and the impingement point of the second reflected radiation beam. The method further includes altering the first incidence angle to a second incidence angle ($A_2$) and measuring the distance ($d_2$) between the impingement point of a third reflected beam and the impingement point of a fourth reflected beam on the detection device. The method finally provides for obtaining the sample thickness L and sample index of refraction n from the following equations:

$$d_1 = [2 \cdot L/n] \cdot [\sin A_1/(1-(\sin^2 A_1)/n^2)^{1/2}] \text{ and}$$

$$d_2 = [2 \cdot L/n] \cdot [\sin A_2/(1-(\sin^2 A_2)/n^2)^{1/2}]$$

Another method for the simultaneous determination of a sample thickness L and index of refraction n, is also provided which involves transmitting the radiation beam through the sample, and intercepting the transmitted radiation beam by the detection device and measuring the distance ($d_1$) between the point on the detection device where the axis intercepts the detection device and the point on the detection device where the transmitted beam impinges on the detection device. This method also includes directing the radiation beam along a second axis with the sample, and transmitting the radiation beam through the sample and measuring a second distance ($d_2$) between a point on the detection device where the second axis intercepts the detection device and a point on the detection device where the transmitted beam impinges on the detection device. This method involves solving the following system of equations for transmitted radiation beams:

$$d_1 = L[\sin A_1 - (\sin 2A_1 \div 2(n^2 - \sin^2 A_1)^{1/2})] \text{ and}$$

$$d_2 = L[\sin A_2 - (\sin 2A_2 \div 2(n^2 - \sin^2 A_2)^{1/2})]$$

to obtain values for L and n.

BRIEF DESCRIPTION OF THE DRAWINGS

The invention can be more fully understood from the following description thereof in connection with the accompanying drawings described as follows.

DETAILED DESCRIPTION OF THE INVENTION

Figure 1:
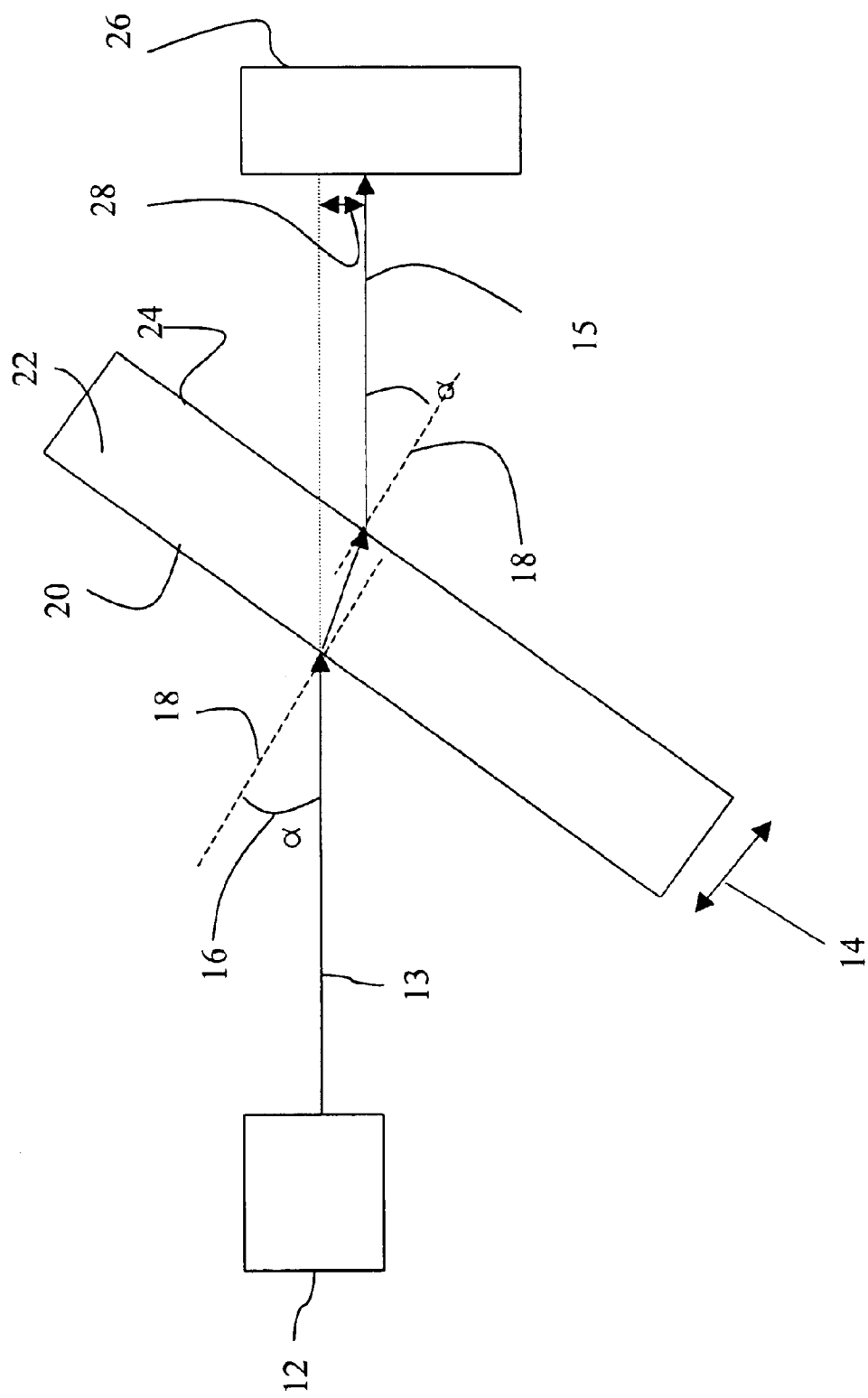
FIG. 1 is a schematic view of a light beam transmitted through a film.

The method and apparatus of the present invention provide for the simultaneous measurement of a film thickness and index of refraction by using a photo detector and applying Snell's Law of refraction.

By using photoimaging, such as with a charge coupled device (CCD), the present invention allows measuring the refractive index (n) and the local thickness (L) of flat samples such as glass, sapphire, quartz or plastic windows. The materials to be measured are preferably transparent in the visible region of radiation. This technique is based on the deflection property of an oblique laser beam when crossing a material with a different refractive index than that of the medium in which it is located. Typically the measurement of the properties of materials is done in an atmosphere of air, which has a refractive index of one ($n_{air}$=1). The material being measured typically has a refractive index greater than one, and the change of refractive index at the air-material interface causes a change in the direction of propagation of the light beam.

A change in propagation direction, or deflection, occurs at two air-material interfaces of the sample studied, the interface as the light beam enters the material, and the interface when the light beam exits the material. If the laser beam forms an incident angle with the vector normal to the material surfaces, the amount of deflection is a function of the incident angle, the refractive index of the material, and the thickness of the material.

By using Snell's law of refraction at each air-material interface, $n_1 \sin \theta_1 = n_2 \sin \theta_2$, where the subscripts 1 and 2 stand for the incident media (air) and the sample material, respectively, an expression for the beam displacement can be derived. For the purposes of this derivation, the two air-material interface surfaces of the samples are considered to be at least locally parallel. If the interface surfaces are parallel than $\theta_1$ and $\theta_2$ are the same angle, referred to hereafter as $\alpha$. The application of Snell's law to the film configuration provides the following expression:

$$d = L \cdot \left[ \sin\alpha - \frac{\sin 2\alpha}{2 \cdot \sqrt{N^2 - \sin^2\alpha}} \right] \quad \text{EQN. 1}$$

Equation 1 relates the thickness of the sample material, L, and the refractive index of the material, n, to the incidence angle, $\alpha$, and the deflected beam displacement, d. It's clear that if either L or n is known than the other parameter can be directly estimated through EQN 1. However, when the two parameters, L and n, are both unknown, interferometric techniques are typically used to estimate the optical constants simultaneously.

However, if at least two measurements are performed at two different incident angles, $\alpha_1$ and $\alpha_2$, L and n can be simultaneously measured directly using a photodetector device that can measure $d_1$ and $d_2$, such as a CCD camera.

The invention will next be described with reference to the figures in which same numbers indicate same parts in all figures. The figures are provided to facilitate the description of the invention and are not exact representations to scale of the different elements depicted nor do they show additional elements that are not essential in describing the present invention.

The deflection phenomenon exploited by the present invention is diagramed in FIG. 1. A light beam source 12, such as a laser, provides an incident light beam 13 on a film sample 22. The two faces of the sample 20 and 24 are parallel, at least locally for the light beam, and therefore the beam is deflected by the film, and exits the film in a beam 15 parallel to the incident beam 13.

The incident beam 13 makes an angle 16, labeled herein as $\alpha$, with a vector 18 normal to the film surface 20. Measurement of transmitted light from a light source polarized in the incidence plane should be achieved with incident angles corresponding to an internal angle (on the second interface) smaller than the total internal reflection angle. An incident angle corresponding to the Brewster angle is preferable in this case. With non-polarized beam sources, any incident angle provides a transmitted beam 15. The transmitted beam is deflected while propagating through the thickness of the film 14 because of the film has a different index of refraction. The transmitted beam is again deflected at the material-air interface at the second film surface 24. The transmitted beam 15 forms the same angle $\alpha$ with the vector normal to the second surface of the film 24. The deflection of the beam while propagating through the film is a function of the index of refraction of the film material and the thickness of the material, as well as the incident angle. The deflection can be measured as the distance between the parallel trajectories 28 of the incident beam 13 and the transmitted beam 15. As shown in FIG. 1, a detector is positioned to intercept the non-deflected beam 13, as well as the deflected beam 15.

One method for the simultaneous determination of a sample thickness L and index of refraction n, provided herein is based in part on the principles illustrated in FIG. 1. Since both n and L are unknowns in EQN 1, two measurements of deflection 28, collected at two different incident angles $\alpha$, provides two expressions that satisfy EQN 1 with two remaining unknowns, n and L. With at least two measurements, the expressions can be solved for accurate values of both n and L.

The method includes directing a radiation beam along an axis to form a first angle ($A_1$) with the sample 22. The transmitted radiation beam intercepts a detection device, which measures beam deflection as the distance ($d_1$) between the point of the radiation beam axis and the point of the transmitted beam.

A second measurement is collected by directing the radiation beam along a second axis forming a second angle ($A_2$) with the sample. Again the transmitted beam intercepts the detection device and a second distance ($d_2$) between the point the second axis and the point of the transmitted beam is measured. With the angle and deflection data collected ($A_1$, $A_2$, $d_1$, and $d_2$), the following system of equations, from EQN. 1 may be solved:

$$d_1 = L[\sin(A_1) - (\sin(2A_1) \div 2(n^2 - \sin^2(A_1))^{1/2})] \text{ and}$$

$$d_2 = L[\sin(A_2) - (\sin(2A_2) \div 2(n^2 - \sin^2(A_2))^{1/2})]$$

to obtain values for L and n.

Figure 2:
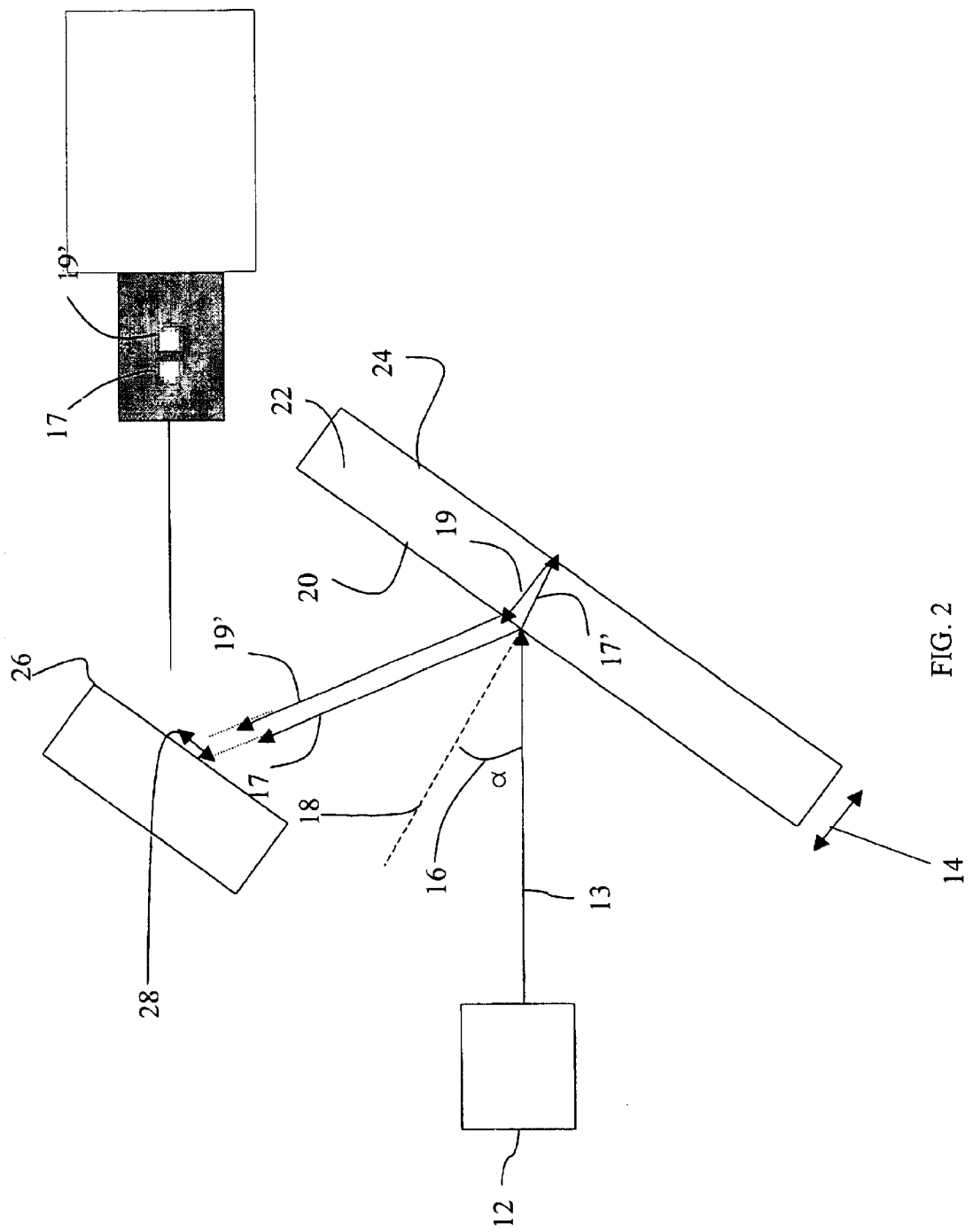
FIG. 2 is a schematic view of a light beam reflected by a film.

A similar method can be used to obtain L and n values by measuring the deflection of radiation beams reflected off a film sample. Such a measurement arrangement is shown schematically in FIG. 2. A radiation source 12 transmits a beam 13 at an incident angle 16 to a vector 18 normal to the surface 20 of the film sample 22.

The beam is partially reflected at the first surface of the film sample 17, and the position of the reflected beam is measured at a detector 26. The beam 13 is also partially transmitted 17' through the width of the sample 14. The transmitted beam 17' is deflected during propagation through the sample due to the change of index of refraction as discussed above. The transmitted beam 17' encounters the second surface 24 of the sample, and a portion of the transmitted beam 19 is reflected off the second surface 24.

The beam reflected off the second surface 19 encounters the first surface of the sample 20, and a portion of the beam is transmitted through the surface of the sample, encountering another change in the index of refraction. This transmitted beam 19' is parallel to the first reflected beam 17, and the position of the resulting beam 19' is measured at the detector 26. The amount of deflection is measured as a distance 28 between the two positions from the reflected beams 17 and 19'.

The angle of reflection is dictated by the angle of incidence, as the angle of reflection equals the angle of incidence, so that there is only a single angle contributing to the calculation of L and n using measurements collected through beam reflection.

A method for the simultaneous determination of a sample thickness L and index of refraction n, by measuring the position of reflected radiation beams includes transmitting a radiation beam onto the sample at a first incidence angle ($A_1$) relative to an axis 18 perpendicular to the first surface 20 of the sample. The beam is reflected from both the first 20 and second 24 surfaces of the sample and generates first 17 and second 19' reflected radiation beams. A detection device 26 measures the relative positions of the first and second reflected radiation beams. From the relative positions, a distance ($d_1$) on the detector can be measured. A second measurement is taken by altering the first incidence angle ($A_1$) to a second incidence angle ($A_2$) and again measuring the distance ($d_2$) between a third reflected beam and a fourth reflected beam on the detection device. Values for the sample thickness L and sample index of refraction n can then be calculated using the following expressions, derived from Snell's law for reflected beams:

$$d_1 = [2L/n][\sin(A_1) + (1-(\sin^2(A_1))/n^2)^{1/2}] \text{ and}$$

$$d_2 = [2L/n][\sin(A_2) + (1-(\sin^2(A_2))/n^2)^{1/2}].$$

As with the transmitted beam calculation, measurements obtained at two incident angles provide the above two equations with two unknowns, which can be solved directly.

Figure 3:
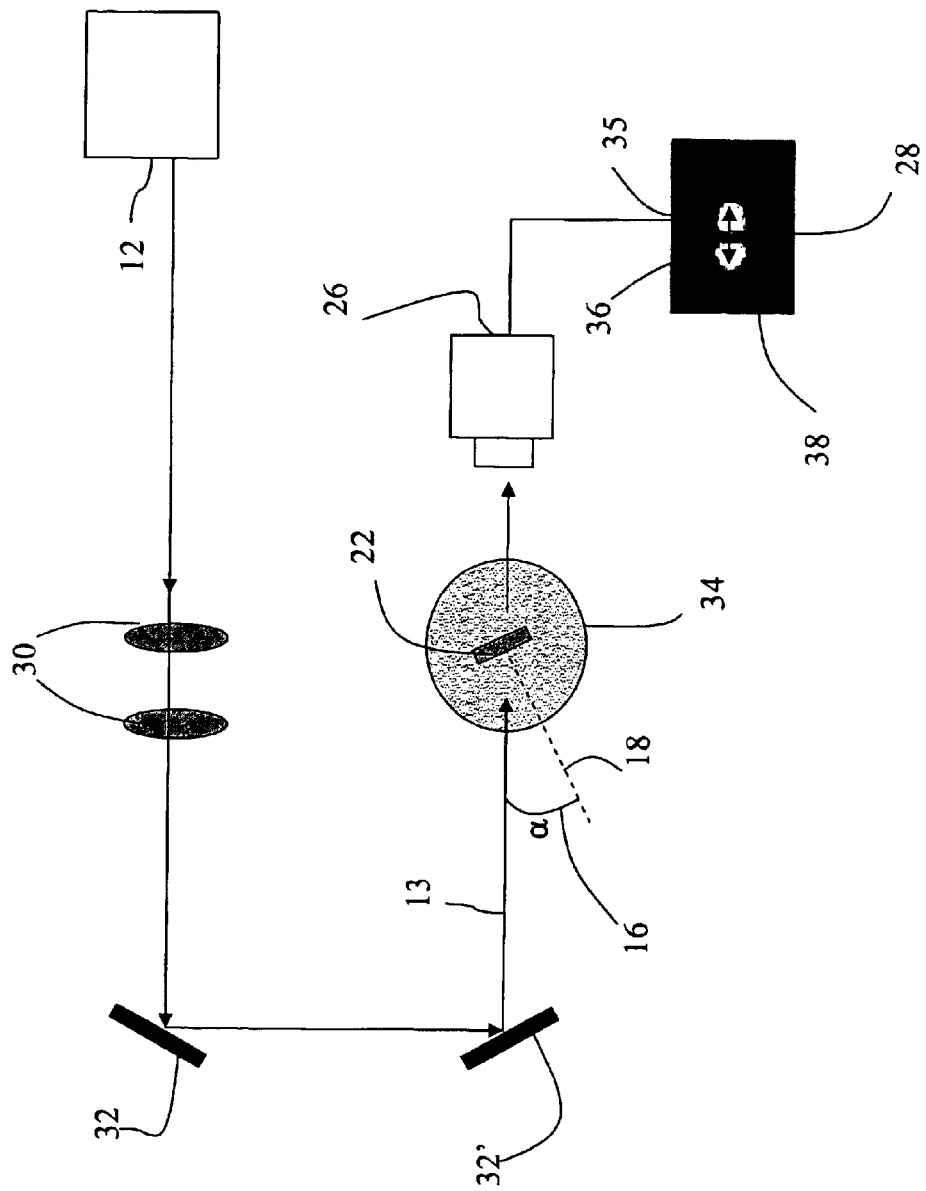
FIG. 3 is a schematic view of a measurement apparatus of the present invention.

An exemplary apparatus for collecting these measurements is shown schematically in FIG. 3. A radiation source 12 provides a beam which may be polarized using polarization optics 30, and directed towards a sample 22 using a series of optical mirrors 32 and 32'. The sample 22 is secured onto a sample stage 34, that can rotate about an axis to vary the angle 16 between the vector 18 normal to the sample surface. The sample stage also allows for easy transfer of samples, such as on a production line. When measurements are performed in the transmission mode, as shown in FIG. 3, the non-deflected beam position may be gathered when the sample stage does not contain a sample, either before or after samples are loaded onto the stage. Alternate configurations may include a sample with a fixed position with optics, or multiple sources providing radiation beams at various angles to the sample surface. The radiation sources and the detectors may also move in space to optimize the collection of beam deflection data.

The exemplary apparatus in FIG. 3 shows a detector 26 positioned to intercept the non-deflected and deflected transmitted beams, and connected to a computer with a display 38 to show the positions of the deflected and non-deflected beams 35 and 36, and the measured distance between the beams 28.

A single beam with a non-rotating sample may also be used by configuring the incident beam with different sagittal and azimuthal angle values α and θ. The corresponding displacements, $d_\alpha$, and $d_\theta$ are then measured horizontally and vertically.

In practice a method using sagittal and azimuthal angle values may express the angle values in a Cartesian coordinate system for convenience. In such a case, a substantially monochromatic collimated radiation beam is transmitted onto the sample along an axis forming a first angle $A_x$ and subsequently a second angle $A_y$ in a coordinate system having the sample in a plane defined by x and y axes. In this system, the angle $A_x$ is measured in a plane defined by the x and z axes and an angle $A_y$ is measured in a plane defined by the y and z axes. The detector can be located in a plane parallel to the x-y plane and the first distance $d_x$ is measured on the x-axis. A second distance $d_y$ can be measured on the y-axis and the measurements used to solve the following equations, as stated above:

$$d_x = L[\sin(A_x) - (\sin(2A_x) \div 2(n^2 - \sin^2(A_x))^{1/2})] \text{ and}$$

$$d_y = L[\sin(A_y) - (\sin(2A_y) \div 2(n^2 - \sin^2(A_y))^{1/2})]$$

to obtain values for L and n. Similar conversion may be performed for the measurements collected in the reflection mode.

The radiation source may be a laser, light emitting diode (LED) or an incoherent source, among others. As such the radiation beam may be monochromatic, and or collimated, however sources need not be either monochromatic or collimated. Low-coherence and incoherent sources avoid possible interference between the reflected beams, which may influence the exact positioning of the beams' spots on the CCD.

As mentioned above, for measurements in the transmission mode, the incident angle α must lead to an internal angle on the second interface smaller than the total internal reflection angle (Critical angle) when polarized radiation sources are used. For these measurements the radiation beam is preferably at an incident angle α greater than 10 degrees to the sample surface for resolution purposes.

The sample for analysis is described as having a first and a second surface. For film samples, the surfaces are considered to be at least locally parallel. That is that the areas of the first and second sample surfaces that encounter the radiation beam are substantially parallel, even if the surfaces as a whole are not entirely parallel.

This condition of parallel surfaces is accommodated for liquid samples by loading the liquid sample into a cuvette with substantially parallel walls, discussed in more detail below.

The detection device may be a photo-detector which comprises an array of radiation sensors. The accuracy of the measurement of n and L is dependent on the resolution of the detection device. Charge coupled device (CCD) cameras offer high resolution and sensitivity for such applications. The CCD camera can comprise either a single two-dimensional sensor or an array of sensors. A CCD camera and appropriate software can be used to locate the beam spots before and after deflection or reflection. The displacement 28 can be deduced from the center of gravity of the beam spot.

The detection device is preferably positioned so that reflected or transmitted beams are completely intercepted. A minimum lateral distance from the source and the detection device may be calculated for this purpose. The variation in the lateral distance of the transmitted and reflected beams is a function of the incidence angle. Beam divergence values may also be considered when positioning the detection device.

The detection device may be connected to a computer or other data handling device. The computer may be programmed to measure the distances $d_1$, $d_2$, $d_x$ or $d_y$ from the detection device and may further be used to calculate L and n from the appropriate set of equations.

Figure 4:
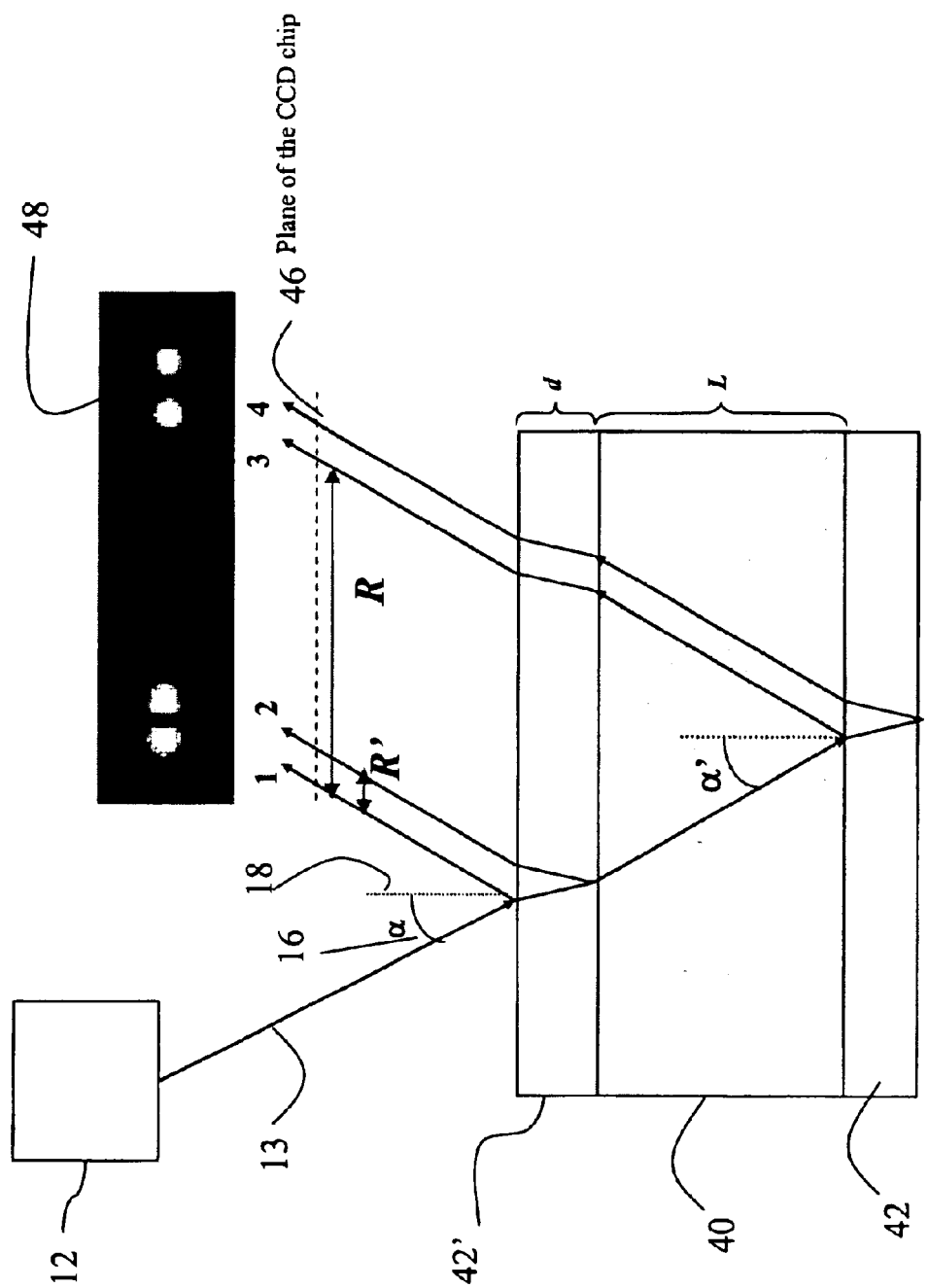
FIG. 4 is a schematic view of a measurement of a liquid sample in a cuvette according to the present invention.

Now referring to FIG. 4, an additional embodiment of the present invention is illustrated wherein the sample is contained in a transparent cuvette. This method employs the same imaging technique as discussed above using reflected beams. This method allows the measurement of other physical constants of fluid samples.

A radiation source 12 transmits a beam 13 at an incident angle 16, and a portion of the beam 1 is reflected of the first cuvette wall 42'. Another portion of the beam 2 is reflected off the cuvette wall 42' to sample 40 interface. Another portion 3 of the same beam is reflected off the interface between the sample 40 and the second cuvette wall 42, and another reflected beam 4 results from a reflection off the cuvette wall 42 to air interface. The total-internal reflection angle on either the cuvette-sample or sample-cuvette interface is avoided when the incident light angle is lower than the critical angle for either interface.

The geometry of the different reflections captured in a detector plane 46, and imaged on a display 48, illustrate how the principle applied to the film samples can be extended to calculate the thickness of the cuvette walls through R' measurement. The measurement of R and R' allows the estimation of the thickness' of the sample cuvette walls and the fluid within in a similar manner as applied above. This extension of Snell's Law includes measuring the relative intensities of beams 1 to 3 to estimate the absorption coefficients of the cell and of the fluid. Further coefficients, such as the reflection and transmission coefficients of each interface can also be estimated using two or more incident beams of various intensities. An intensity-modulated laser beam may be advantageously employed for this purpose.

For optimal performance in measuring L and n, a low-divergence laser beam is preferred. Low-divergence for these purposes is on the order of mrads in magnitude. If higher divergence beams are to be used, the beam sizes should preferably be smaller than the detection matrix dimensions. For CCD camera detectors, the detection matrix dimensions are typically 10×10 m², however 30×30 mm² are currently available in the market. The orientation of the source, sample and detector is preferably optimized in both the transmission and reflection modes to minimize any decrease in detector resolution caused by beam divergence.

The measurement method of the present invention is illustrated by the following examples but is not intended to be limited thereby:

EXAMPLES

An exemplary measurement was preformed with a HeNe laser at 544 nm as the radiation source, and a sample placed on a platform with angular motion capability about the horizontal. The platform was on a rotation stage with free motion of 360° and rotational resolution of 1°. The beam displacement was monitored by a CCD camera with pixel separation of approximately 13 μm and each image was downloaded to a computer. The laser beam was attenuated with two polarizers from its original 1.5 mW to less than 1 μW so as not to saturate the CCD camera.

The displacement d was measured by subtracting the horizontal coordinate of the beam spot on the CCD at $\alpha=0°$ from the similar coordinate at another $\alpha$ value. Two values of d are measured at two different angles for each sample.

The system of two equations derived from EQN. 1 with the two sets $(\alpha_1, d_1)$ and $(\alpha_2, d_2)$ was solved numerically, leading to a unique solution for L and n.

Several samples with different thickness' and refractive indices were analyzed according to this method and the results appear in the following tables for L (Table 1) and n (Table 2).

TABLE 1

The measurements and corresponding errors of the thickness L of each sample.

| $L_{measured}$ (mm) | 0.24 | 0.99 | 1.03 | 3.06 | 3.07 | 5.84 | 10.02 |
|---|---|---|---|---|---|---|---|
| Precision (%) | 3.7 | 1.1 | 2.6 | 1.9 | 2.4 | 2.7 | 1.0 |

TABLE 2

The errors on the measurements of the refractive index n of each sample.

| $N_{measured}$ | 1.48 | 1.51 | 1.58 | 1.60 | 1.60 | 1.61 | 1.74 |
|---|---|---|---|---|---|---|---|
| Precision (%) | 1.3 | 3.2 | 6.8 | 4.1 | 6.4 | 4.7 | 17.0 |

The errors for the thickness estimations are due to a systematic error included by the imaging software. The software used for these examples includes a bias displacement to each spot location when snapping a single image frame. As a result, a relatively high error on the estimation of the displacements was introduced. These errors appear to be more significant in the estimation of the refractive index as the numerical program employed determines n from the estimated value for L. The estimation error is amplified accordingly in the refractive index measurement. Therefore, lower errors on the estimations are expected with software refinement.

Furthermore, a spatial filter may be used in the laser beam path before the sample to generate a smooth gaussian laser beam cross section that may be fitted correctly with a software to allow precise localization of the beam spot on the CCD camera.

Those having the benefit of the above description of my invention may provide numerous such modifications of the invention. These modifications are to be construed as being encompassed within the scope of the present invention as set forth in the appended claims.

What is claimed is:

1. A method for the simultaneous determination of a sample thickness L and index of refraction n, the method comprising:
   a) forming said sample with a first and a second surfaces, wherein the first and second surfaces are substantially locally flat;
   b) forming a radiation beam and impinging said radiation beam onto said sample at a first incidence angle $A_1$ relative to an axis perpendicular to said first surface;
   c) reflecting said impinged radiation beam from said first and said second surfaces of said sample forming a first and a second reflected radiation beams;
   d) impinging said first and second reflected radiation beams on a detection device;
   e) measuring a distance $d_1$ on said detection device between an impingement point of said first reflected beam and an impingement point of said second reflected radiation beam;
   f) altering said first incidence angle to a second incidence angle $A_2$ and again measuring a distance $d_2$ between an impingement point of a third reflected beam and an impingement point of a fourth reflected beam on said detection device;

g) obtaining the sample thickness L and sample index of refraction n from the following equations:

$$d_1 = [2L/n] \cdot [\sin A_1/(1-(\sin^2 A_1)/n^2)^{1/2}] \text{ and}$$

$$d_2 = [2L/n] \cdot [\sin A_2/(1-(\sin^2 A_2)/n^2)^{1/2}].$$

2. A method for the simultaneous determination of a sample thickness L and index of refraction n, the method comprising reflecting a radiation beam at a first incidence angle $A_1$ onto a sample having a first and a second parallel reflective surfaces, wherein the first and second surfaces are substantially locally flat, and projecting a first surface reflected radiation beam and a second surface reflected radiation beam onto a detection device, determining a distance $d_1$ between said projected reflection beams onto said detection device, altering said incidence angle to a second incidence angle $A_2$ and measuring a second distance $d_2$ between said projected reflection beams onto said detection device, and solving the following system of equations:

$$d_1 = [2L/n] \cdot [\sin A_1/(1-(\sin^2 A_1)/n^2)^{1/2}] \text{ and}$$

$$d_2 = [2L/n] \cdot [\sin A_2/(1-(\sin^2 A_2)/n^2)^{1/2}]$$

to obtain values for L and n.

3. A method for the simultaneous determination of a sample thickness L and index of refraction n, the method comprising:
   a) directing along an axis forming a first angle $A_1$ with said sample a radiation beam, transmitting said radiation beam through said sample, intercepting said transmitted radiation beam by a detection device and measuring a distance $d_1$ between a point on said detection device where said axis intercepts said detection device and a point on said detection device where said transmitted beam impinges on said detection device; and
   b) directing said radiation beam along a second axis forming a second angle $A_2$ with said sample, again transmitting said radiation beam through said sample and measuring a second distance $d_2$ between a point on said detection device where said second axis intercepts said detection device and a point an said detection device where said again transmitted beam impinges on said detection device; and
   c) solving the following system of equations:

$$d_1 = L[\sin A_1 - (\sin 2A_1 \div 2(n^2 - \sin^2 A_1)^{1/12})] \text{ and}$$

$$d_2 = L[\sin A_2 - (\sin 2A_2 \div 2(n^2 - \sin^2 A_2)^{1/2})]$$

to obtain values for L and n.

4. The method according to any one of claims 1–3 wherein the detection device comprises a photo-detector.

5. The method according to any one of claims 1–3 wherein angle $A_1$ and angle $A_2$ are both greater than 10 degrees.

6. The method according to any one of claims 1–3 wherein the radiation beam is monochromatic.

7. The method according to any one of claims 1–3 wherein the radiation beam is collimated.

8. The method according to any one of claims 1–3 wherein the radiation beam is a laser beam.

9. The method according to any one of claims 1–3 wherein the sample transmits a portion of the radiation beam.

10. The method according to any one of claims 1–3 wherein the sample is a liquid in a cuvette.

11. The method according to any one of claims 1–3 wherein the first and the second surfaces of the sample are parallel.

12. The method according to any one of claims 1–2 wherein the radiation beam is polarized and the incidence angles $A_1$ and $A_2$ both correspond to internal angles smaller than a total internal reflection angle at each of said surfaces.

13. A method for the simultaneous determination of a sample thickness L and index of refraction n, the method comprising:
   a) directing a substantially monochromatic collimated beam of radiation onto said sample along an axis forming a first angle $A_x$ and a second angle $A_y$ in a coordinate system having said sample in a plane defined by the x and y axis of said system, wherein said $A_x$ is measured in a plane defined by the x and z axes and $A_y$ in a plane defined by the y and z axes,
   b) transmitting said beam through said sample and impinging said transmitted beam onto an array of radiation detectors arrayed in a plane parallel to said x-y plane;
   c) measuring a first distance $d_x$ on the x-axis between a point where said axis of monochromatic collimated beam impinges on said array of radiation detectors and a point where the monochromatic collimated beam impinges on said array of radiation detectors,
   d) measuring a second distance $d_y$ on the y-axis between a point where said axis of monochromatic collimated beam impinges on said array of radiation detectors and a point where the monochromatic collimated beam impinges on said array of radiation detectors; and
   e) solving the following system of equations:

$$d_x = L[\sin A_x - (\sin 2A_x \div 2(n^2 - \sin^2 A_x)^{1/2})] \text{ and}$$

$$d_y = L[\sin A_y - (\sin 2A_y \div 2(n^2 - \sin^2 A_y)^{1/2})]$$

to obtain values for L and n.

14. A method for the simultaneous determination of a sample thickness L and index of refraction n, the sample having substantially parallel first and second surfaces lying in an x-y plane of a Cartesian co-ordinate system having x, y and z axes, the two surfaces separated by said distance L measured along the z axis, the method comprising:
   a) directing an incident radiation beam of substantially collimated monochromatic radiation onto said sample, said radiation beam forming an angle Ax in the x-z plane and an angle Ay in the y-z plane relative to the z axis;
   b) reflecting said incident radiation off said first and said second surfaces;
   c) intercepting said reflected incident radiation from said first and second surfaces with an array of radiation sensors and determining a first distance $d_x$ and a second distance $d_y$ between a point of incidence on said array of radiation sensors of said radiation beam reflected from said first surface and a point of incidence of said radiation beam reflected off said second surface measured along said x axis and said y axis respectively; and
   d) solving the following equations simultaneously for said thickness L and said index of refraction n:

$$d_x = [2L/n] \cdot [\sin A_x/(1-(\sin^2 A_x)/n^2)^{1/2}] \text{ and}$$

$$d_y = [2L/n] \cdot [\sin A_y/(1-(\sin^2 A_y)/n^2)^{1/2}].$$

15. The method according to claims 13 or 14 wherein said array of radiation sensors is a single two dimensional CCD sensor or an array of CCD sensors.

16. The method according to claims 13 or 14 wherein said array of radiation sensors is connected with a computer and said computer is programmed to measure the distances $d_x$ or $d_y$ on said array of radiation sensors.

17. The method according to claim 16 wherein said computer is also programmed to solve said equations for L and n.

18. A system for the simultaneous determination of a sample thickness L and index of refraction n, the sample having substantially parallel first and second surfaces, comprising:

a) a radiation beam along a path;

b) a holder adapted to hold said sample in said beam path at an adjustable angle relative to said sample surfaces;

c) a radiation detector placed to receive said radiation beam after said beam has impinged on said sample, the radiation detector comprising an array of sensors;

d) measuring means for measuring a distance between a reference point on said radiation detector and a point of impingement of said beam on said radiation detector e) means for outputting an output indicative of the sample thickness L and index of refraction n, wherein the output indicative of the sample thickness and index of refraction is determined from the distance measured by the measuring means.

19. The system of claim 18 wherein the sample is a liquid in a cuvette.

* * * * *

UNITED STATES PATENT AND TRADEMARK OFFICE
CERTIFICATE OF CORRECTION

PATENT NO. : 6,731,380 B2
DATED : May 4, 2004
INVENTOR(S) : Mohamed Kamel Amara, Noureddine Melikechi and Sabbir M. Mian It is certified that error appears in the above-identified patent and that said Letters Patent is hereby corrected as shown below:

Column 10,
Line 46, delete "Ax" and insert -- $A_x$ --
Line 47, delete "Ay" and insert -- $A_y$ --

Signed and Sealed this

Thirtieth Day of November, 2004

JON W. DUDAS
*Director of the United States Patent and Trademark Office*